United States Patent
Yang et al.

(10) Patent No.: US 11,940,431 B2
(45) Date of Patent: Mar. 26, 2024

(54) DETECTION METHOD FOR DETERMINING CONTENT OF CHLORINE IONS IN MARINE SAND

(71) Applicant: FUZHOU UNIVERSITY, Fuzhou (CN)

(72) Inventors: Zhengxian Yang, Fuzhou (CN); Rongcan Hong, Fuzhou (CN); Lin Lu, Fuzhou (CN); Shuikun Cai, Fuzhou (CN); Deng Changtai, Fuzhou (CN); Xiaohui Lin, Fuzhou (CN); Xiuqing Lin, Fuzhou (CN)

(73) Assignee: FUZHOU UNIVERSITY

( * ) Notice: Subject to any disclaimer, the term of this patent is extended or adjusted under 35 U.S.C. 154(b) by 0 days.

(21) Appl. No.: 17/290,784

(22) PCT Filed: Jul. 17, 2020

(86) PCT No.: PCT/CN2020/102548
§ 371 (c)(1),
(2) Date: May 3, 2021

(87) PCT Pub. No.: WO2021/036570
PCT Pub. Date: Mar. 4, 2021

(65) Prior Publication Data
US 2022/0412930 A1    Dec. 29, 2022

(30) Foreign Application Priority Data
Aug. 28, 2019 (CN) .......................... 201910802795.0

(51) Int. Cl.
*G01N 1/28* (2006.01)
*G01N 1/34* (2006.01)
*G01N 1/40* (2006.01)
*G01N 31/16* (2006.01)

(52) U.S. Cl.
CPC .............. *G01N 31/16* (2013.01); *G01N 1/28* (2013.01); *G01N 1/34* (2013.01); *G01N 1/4077* (2013.01)

(58) Field of Classification Search
CPC .. G01N 1/00; G01N 1/28; G01N 1/34; G01N 1/38; G01N 1/40; G01N 1/4005; G01N 1/4077; G01N 2001/4088; G01N 2001/386; G01N 2001/388; G01N 31/00; G01N 31/02; G01N 31/16; G01N 31/18; G01N 31/22; G01N 31/227; G01N 33/24
See application file for complete search history.

(56) References Cited

FOREIGN PATENT DOCUMENTS

| CN | 101614718 A | * | 12/2009 | |
|----|-------------|---|---------|---|
| CN | 104634856 A | * | 5/2015  | |
| CN | 107727791 A | * | 2/2018  | ............. G01N 27/44 |
| CN | 207147980 U | * | 3/2018  | |

OTHER PUBLICATIONS

CN-107727791-A—Translate (Year: 2018).*
CN-207147980-U—translate (Year: 2018).*
CN-104634856-A—translate (Year: 2015).*
CN-101614718-A—translate (Year: 2009).*

* cited by examiner

*Primary Examiner* — Kristina M Deherrera
*Assistant Examiner* — Fatemeh Esfandiari Nia
(74) *Attorney, Agent, or Firm* — Jose Cherson Weissbrot

(57) ABSTRACT

A detection method for determining chloride ions content in sea sand includes the steps of drying sea sand to a constant weight, adding the dried sea sand to boiling deionized water, fully stirring, and standing and filtering the deionized water to obtain washed sea sand and a washed filtrate. The washed sea sand is then ground into a powder and added into deionized water and fully stirred, the deionized water then filtered to obtain a powder filtrate. Half of the washed filtrate and half of the powder filtrate is then mixed and stirred to prepare a mixed filtrate. The chloride ions content in each of the washed filtrate, the powder filtrate, and the mixed filtrate is then measured by using a silver nitrate titration method. The detection results are then analyzed and corrected to obtain the chloride ions content in the sea sand.

5 Claims, No Drawings

DETECTION METHOD FOR DETERMINING CONTENT OF CHLORINE IONS IN MARINE SAND

BACKGROUND OF THE INVENTION

1. Technical Field

The present invention belongs to the technical field of the detection of chloride ions content, and in particular, relates to a detection method for determining chloride ions content in sea sand.

2. Description of Related Art

At present, sand and gravel resources show a trend of gradual decline or even exhaustion. With good grain form, low cost, low mud content and abundant reserves, sea sand is a better substitute for river sand. The rational use of the sea sand is of great significance to the construction of infrastructures and the sustainable development of society. However, impurities such as chloride salts are present in the sea sand, and the chloride salts may accelerate the corrosion of reinforcing steel bars and greatly reduce the durability of concrete structures. The actual engineering survey found that damage to concrete structures caused by chloride ions is still common. This is mainly due to the many problems occurred during the detection of chloride ions content in the purified sea sand, which are summarized as follows:

(1) The sea sand to be detected has been treated improperly. Specifically, the sea sand is often incompletely treated with the current method for detecting the chloride ions content; this is mainly due to the tact that the chloride ions in the fissures and pores of the sea sand are kept in a stable state due to the tight wrapping of organic matters in the ocean, and the chloride ions remaining in the fissures and pores of the sea sand cannot be released by using methods such as normal-temperature immersion or oscillation. In this context, the measured value of chloride ions content in the sea sand is significantly lower than the actual value; and problems endangering the structural safety of buildings will be caused if such sand is applied in construction projects.

(2) The method for preparing the filtrate to be detected is less targeted. Specifically, a filtrate to be detected for chloride ions can be obtained either by purifying the sea sand with fresh water or by grinding and filtering the sea sand, but the sea sand is greatly different in grain size and chloride ions concentration before and after being ground and crushed; and if the filtrate to be detected is prepared with the same method, the incomplete dissolution of the chloride ions may be caused, which would finally affect the detection results on the chloride ions content.

(3) The detection results are difficult to correct due to the lack of references. Specifically, during the detection of chloride ions, the same solution is often detected once or multiple times, but only an arithmetic mean value is simply calculated even for multiple detections. Therefore, the detection results cannot be crossly referred and compared in most cases, making the detection errors difficult to be corrected.

(4) Common methods for detecting the chloride ions take a long time, and operators may easily feel tired after a long-term experiment, which increases the probability of experimental errors.

Therefore, it is of great significance to optimize the detection method for determining the chloride ions content in the sea sand according to actual needs.

BRIEF SUMMARY OF THE INVENTION

To solve the problems existing in the prior art, the present invention provides a detection method capable of accurately measuring the chloride ions content in sea sand. In said detection method, a sea sand sample is treated in steps; hen different filtrates to be detected of the same sea sand sample are detected in the mass of chloride ions; and the detection results are compared, analyzed and corrected, which significantly improves the accuracy of the detection results.

In order to achieve the object above, the present invention is implemented through the following technical solution: a detection method for determining chloride ions content in sea sand. The method is performed as follows:

Step 1, preparing a washed filtrate:

drying a sea sand sample to be detected to constant weight, weighing the dried sea sand sample to be detected with a mass of $G_0$, then adding the dried sea sand sample to boiling deionized water, fully stirring for 3-6 min, letting stand for 10-15 min, then filtering to obtain washed sea sand and a washed filtrate, wherein the deionized water is heated during stirring to keep the temperature not lower than 90° C., besides, a mass ratio of the dried sea sand sample to be detected for mixing and stirring to the deionized water is 1:(1.5-2.5);

Step 2, preparing a powder filtrate:

drying the washed sea sand from Step 1 until the surface is free of water, then grinding the washed sea sand into powder with a fineness of not less than 100 meshes, then adding the powder to deionized water, fully stirring for 5-10 min, and afterwards filtering to obtain a powder filtrate, wherein a mass ratio of the dried washed sea sand to the deionized water is 1:(1.5-2.5);

Step 3, preparing a mixed filtrate:

firstly, placing the washed filtrate prepared in Step 1 and the powder filtrate prepared in Step 2 in a thermostatic chamber and letting stand for 15-20 min; then dividing the washed filtrate from Step 1 after standing into 2 equal parts separately, dividing the powder filtrate prepared in Step 2 after standing into 2 equal parts separately, and then mixing one part of the washed filtrate and one part of the powder filtrate to obtain a mixed filtrate, wherein the remaining part of the washed filtrate and the remaining part of the powder filtrate are for later separate use respectively;

Step 4, measuring the mass of chloride ions in different filtrates:

taking the mixed filtrate, the remaining part of the washed filtrate and the remaining part of the powder filtrate from Step 3 in same volume, and measuring the mass $H_1$ of chloride ions in the remaining part of washed filtrate, the mass $H_2$ of chloride ions in the remaining part of powder filtrate and the mass $H_3$ of the chloride ions in the mixed filtrate by using a silver nitrate titration method;

Step 5, determining the chloride ions content in the sea sand:

firstly, calculating the value of a, wherein a is the ratio of a sum of the mass $H_1$ of chloride ions in the remaining part of washed filtrate as measured in Step 4 and the mass $H_2$ of chloride ions in the remaining part of powder filtrate as measured in Step 4 to the mass $H_3$ of chloride ions in the mixed filtrate as measured in Step 4, i.e., $a=(H_1+H_2)/H_3$;

then, when $0.850 \leq a \leq 1.150$ directly determining the chloride ions content Q in the sea sand according to the following three conditions; when the value of a is less than 0.850 or the value of a is greater than 1.150, repeating Step 4 and recalculating the value of a until $0.850 \leq a \leq 1.150$, and then determining the content Q of chloride ions in the sea sand according to the following three conditions:

Condition 1: when $0.850 \leq a < 0.975$, the total mass H of chloride ions in the sea sand is: $H=m(H_1+H_2)+H_3$; and then the chloride ions content Q in the sea sand is:

$$Q = \frac{m(H_1 + H_2) + H_3}{G_0} \times 100\%;$$

Condition 2: when $0.975 \leq a < 1.025$, the total mass H of chloride ions in the sea sand is: $H=H_1+H_2+H_3$; and then the chloride ions content Q in the sea sand is:

$$Q = \frac{H_1 + H_2 + H_3}{G_0} \times 100\%;$$

Condition 3: when $1.025 \leq a < 1.150$, the total mass H of chloride ions in the sea sand is: $H=H_1+H_2+nH_3$; and then the chloride ions content Q in the sea sand is:

$$Q = \frac{H_1 + H_2 + nH_3}{G_0} \times 100\%;$$

wherein m and n are coefficients, with $m=1+(1-a)=2-a$, and $n=1+(a-1)=a$.

Further, after the mixed filtrate is prepared in Step 3, the remaining part of the washed filtrate and the remaining part of the powder filtrate are placed in the same thermostatic chamber. The mixed filtrate, the washed filtrate and the powder filtrate must be at the same temperature during detection. As a result, the uniformity in detection results of the respective filtrates can be guaranteed.

Further, when the masses of chloride ions in different filtrates are measured by using the silver nitrate titration method in Step 4, a potassium chromate aqueous solution with a mass fraction of 5% is used as an indicator, and a ratio of a dropped volume of the potassium chromate aqueous solution to the volume of each of the mixed filtrate, the remaining part of the washed filtrate and the remaining part of the powder filtrate during titration is 1:50.

Further, a drying oven with a temperature of 100-110° C. is used for drying in Step 1 and Step 2; and the temperature of the thermostatic chamber is controlled to be 25-35° C. in Step 3.

Further, a magnetic stirrer is used for stirring in Step 1 and Step 2, wherein a revolving speed of the magnetic stirrer is 800-1500 r/min, and the maximum heating temperature of the magnetic stirrer is 120° C. during stirring.

The present invention has the following advantageous effects.

1. According to the present invention, the sea sand is washed with water and filtered at first to avoid the loss of chloride ions on the surface of the sea sand due to direct crushing; then, the washed sea sand is crushed to promote the release of the chloride ions in the tight-wrapping surface films and fissures of the sea sand to a greater extent (due to long-term deposition in the sea, the surface of the sea sand has formed a film layer covered with marine organic matter); and the sea sand is treated in steps in a targeted way to provide a scientific guarantee for the authenticity of the detection results on the chloride ions content.

2. The filtrate to be detected is prepared by using different methods before and after the sea sand is ground according to the present invention, which dissolves the chloride ions to be great extent while dramatically reducing the detection time and decreasing the errors in detecting the chloride ions content.

3. The present invention detects different filtrates as obtained from the same sea sand sample respectively to obtain the mass of chloride ions, and then compares, analyzes and corrects the detection results, which significantly improves the accuracy of the detection results on the chloride ions content.

DETAILED DESCRIPTION OF THE INVENTION

The present invention provides a detection method for determining chloride ions content in sea sand. To further set forth the employed technical means and the effects of the present invention, the present invention will be illustrated in detail below in conjunction with the detailed embodiments.

I. DETAILED DESCRIPTION OF THE INVENTION

A detection method for determining chloride ions content in sea sand according to an embodiment is performed in the steps as follows:

Step 1, preparing a washed filtrate:
drying a sea sand sample to be detected to constant weight, weighing the dried sea sand sample to be detected with a mass of G0, then adding the dried sea sand sample to the boiling deionized water, fully stirring for 3-6 min, letting stand for 10-15 min, and then filtering to obtain washed sea sand and a washed filtrate, wherein the deionized water is heated during stirring to keep the temperature not lower than 90° C., and a mass ratio of the dried sea sand sample to be detected for mixing and stirring to the deionized water is 1:(1.5-2.5);

Step 2, preparing a powder filtrate:
drying the washed sea sand from Step 1 until the surface is free of water, then grinding the washed sea sand into sea sand powder with a fineness of not less than 100 meshes, then adding the sea sand powder to deionized water, fully stirring for 5-10 min, and afterwards, filtering to obtain a powder filtrate, wherein a mass ratio of the dried washed sea sand to the deionized water is 1:(1.5-2.5);

Step 3, preparing a mixed filtrate:
firstly, placing the washed filtrate prepared in Step 1 and the powder filtrate prepared in Step 2 in a thermostatic chamber, and letting stand for 15-20 min; then dividing the washed filtrate from Step 1 after standing into 2 equal parts separately, dividing the powder filtrate prepared in Step 2 after standing into 2 equal parts separately, and then mixing one part of the washed filtrate and one part of the powder filtrate to obtain a mixed filtrate, wherein the remaining part of the washed filtrate and the remaining part of the powder filtrate are for later separate use respectively;

Step 4, measuring the mass of chloride ions in different filtrates:
taking the mixed filtrate, the remaining part of the washed filtrate and the remaining part of the powder filtrate from Step 3 in same volume, and measuring the mass $H_1$ of chloride ions in the remaining part of washed filtrate, the mass $H_2$ of chloride ions in the remaining part of powder filtrate and the mass $H_3$ of the chloride ions in the mixed filtrate by using a silver nitrate titration method;

Step 5, determining chloride ions content in the sea sand:
firstly, calculating the value of a, wherein a is a ratio of a sum of the mass $H_1$ of chloride ions in the remaining part of washed filtrate as measured in Step 4 and the mass $H_2$ of chloride ions in the remaining part of powder filtrate as measured in Step 4 to the mass $H_3$ of chloride ions in the mixed filtrate as measured in step 4, i.e., $a=(H_1+H_2)/H_3$;

then, when $0.850 \leq a \leq 1.150$, directly determining the chloride ions content Q in the sea sand according to the following three conditions; when the value of a is less than 0.850 or the value of a is greater than 1.150, repeating Step 4 and recalculating the value of a until $0.850 \leq a \leq 1.150$, and then determining the chloride ions content Q in the sea sand according to the following three conditions:

Condition 1: when $0.850 \leq a < 0.975$, the total mass H of chloride ions in the sea sand is: $H=m(H_1+H_2)+H_3$; and then the chloride ions content Q in the sea sand is:

$$Q = \frac{m(H_1+H_2)+H_3}{G_0} \times 100\%;$$

Condition 2: when $0.975 \leq a < 1.025$, the total mass H of chloride ions in the sea sand is: $H=H_1+H_2+H_3$; and then the chloride ions content Q in the sea sand is:

$$Q = \frac{H_1+H_2+H_3}{G_0} \times 100\%;$$

Condition 3: when $1.025 \leq a \leq 1.150$, the total mass H of chloride ions in the sea sand is: $H=H_1+H_2+nH_3$; and then the chloride ions content Q in the sea sand is:

$$Q = \frac{H_1+H_2+H_3}{G_0} \times 100\%;$$

wherein m and n are coefficients, with $m=1+(1-a)=2-a$, and $n=1+(a-1)=a$.

Further, after the mixed filtrate is prepared in Step 3, the remaining part of the washed filtrate and the remaining part of the powder filtrate are placed in the same thermostatic chamber. (The mixed filtrate, the washed filtrate and the powder filtrate must be at the same temperature during detection). As a result, the uniformity in detection results of the respective filtrates can be guaranteed.

Further, when the masses of chloride ions in different filtrates are measured by using the silver nitrate titration method in Step 4, a potassium chromate aqueous solution with a mass fraction of 5% is used as an indicator, and a ratio of a dropped volume of the potassium chromate aqueous solution to the volume of each of the mixed filtrate, the remaining part of the washed filtrate and the remaining part of the powder filtrate during titration is 1:50.

Further, a drying oven with a temperature of 100-110° C. is used for drying in Step 1 and Step 2; and the temperature of the thermostatic chamber is controlled to be 25-35° C. in Step 3.

Further, a magnetic stirrer is used for stirring in Step 1 and Step 2, wherein a revolving speed of the magnetic stirrer is 800-1500 r/min, and the maximum heating temperature of the magnetic stirrer is 120° C. during stirring.

Relevant Theoretical Basis:
a formula for calculating the chloride ions content in the sea sand by using the silver nitrate titration method is:

$$Q = \frac{C \times (V-D) \times 0.03545 \times \eta}{G_0} \times 100\%.$$

In the formula, Q represents a percentage content (%) of chloride ions in the sea sand sample to be detected; C represents a concentration (mol/l) of a silver nitrate standard solution; V represents a volume (ml) of the silver nitrate standard solution consumed during titration; D represents a volume (ml) of the silver nitrate standard solution consumed in a blank test; 0.03545 represents a millimolar mass (g/mmol) of chloride ions; and $\eta$ represents a ratio of the total volume of a solution to be detected to the volume of the solution taken during the silver nitrate titration.

Then, the total mass of chloride ions in the sea sand is $H=C \times (V-D) \times 0.03545 \times \eta$; and the chloride ions content in the sea sand sample to be detected is $$Q = \frac{H}{G_0} \times 100\%,$$

After obtaining the washed filtrate, the powder filtrate and the mixed filtrate by using the sea sand sample to be detected, the mass of chloride ions in each of the washed filtrate, the powder filtrate, and the mixed filtrate is calculated by using the silver nitrate titration method, wherein the mass of chloride ions in the washed filtrate is $H_1=C \times (V_1-D) \times 0.03545 \times \eta_1$; the mass of chloride ions in the powder filtrate is $H_2=C \times (V_2-D) \times 0.03545 \times \eta_2$; and the mass of chloride ions in the mixed filtrate is $H_3=C \times (V_3-D) \times 0.03545 \times \eta_3$.

In the formulas above, $V_1$ represents a volume (ml) of the silver nitrate standard solution consumed during the titration of the washed filtrate sample; $V_2$ represents a volume (ml) of the silver nitrate standard solution consumed during the titration of the powder filtrate sample; $V_3$ represents the volume (ml) of the silver nitrate standard solution consumed during the titration of the mixed filtrate sample; $\eta_1$ represents the ratio of the total volume of the washed filtrate to the volume of the washed filtrate solution taken during the silver nitrate titration; $\eta_2$ represents the ratio of the total volume of the powder filtrate to the volume of the powder filtrate taken during the silver nitrate titration; and $\eta_3$ represents the ratio of the total volume of the mixed filtrate to the volume of the mixed filtrate taken during the silver nitrate titration.

II. EMBODIMENTS

Embodiment 1

400 g of sea sand sample to be detected, that was dried to a constant weight, was poured into 800 ml of boiling deionized water, and then fully stirred for 5 min by using a magnetic stirrer at a revolving speed of 1000 r/min. The deionized water was continuously heated during stirring so as to be kept at the temperature of 92° C. Upon completion of the stirring, the deionized water was let stand for 12 min and then filtered to obtain washed sea sand and 580 ml of washed filtrate. The washed sea sand was dried in an oven until the surface was free of water, and then ground into powder with a fineness of 100 meshes by using a ball mill. The powder was poured into 800 ml of deionized water, fully stirred for 10 min and then filtered to obtain 520 ml of powder filtrate. The washed filtrated and the powder filtrate were placed in a thermostatic chamber at 30° C. for 20 min. Then, 290 ml of the washed filtrate and 260 ml of the powder filtrate were taken respectively and then mixed and stirred to obtain 550 ml of mixed filtrate. The mixed filtrate, the washed filtrate and the powder filtrate were placed in the same thermostatic chamber and held at 30° C. for 15 min.

50 ml of the washed filtrate, 50 ml of the powder filtrate and 50 ml of the mixed filtrate were taken with a pipette respectively and added to three different Erlenmeyer flasks. 1.0 ml of potassium chromate solution with a mass fraction of 5% was dropped into each of the three Erlenmeyer flasks containing the washed filtrate, the powder filtrate and the mixed filtrate respectively. A silver nitrate titration method was used to obtain the mass of chloride ions in the washed filtrate as 0.264 g, the mass of chloride ions in the powder filtrate as 0.240 g and the mass of chloride ions in the mixed filtrate as 0.526 g, respectively. Then, the value of a was 0.958, and the chloride ions content in the sea sand was calculated to be 0.263% by using the method shown in Condition 1 according to the present invention.

Comparative Example 1

The chloride ions content in the sea sand was calculated according to the test method in GB/T 14684-2011 Sand for Construction. 1000 g of sea sand sample from the same source as the sea sand sample in the above application Embodiment 1 was dried to a constant weight in the oven and cooled for later use. 500 g of dry sand was weighed and poured into a ground-glass flask. 500 ml of distilled water was added into the ground-glass flask, which was then covered with a stopper, shook once and let stand for 2 h. and then, the ground-glass flak was shook once every 5 min, three times in total. A resulting solution was filtered and measured for the chloride ions content twice by using a silver nitrate titration method, and an athematic mean value of the two test results was calculated to obtain the chloride ions content as 0.135%.

Embodiment 2

400 g of sea sand, that was dried to a constant weight, was poured into 600 ml of boiling deionized water, and then fully stirred for 4 min by using a magnetic stirrer at a revolving speed of 1200 r/min. The deionized water was continuously heated during stirring to be kept at the temperature of 90° C. Upon completion of the stirring, the deionized water was let stand for 10 min and then filtered to obtain washed sea sand and 380 ml of washed filtrate. The washed sea sand was dried in an oven until the surface was free of water, and then ground into powder with a fineness of 120 meshes by using a ball mill. The powder was poured into 600 ml of deionized water, fully stirred for 10 min and then filtered to obtain 350 ml of powder filtrate. The washed filtrate and the powder filtrate were placed in a thermostatic chamber at 30° C. for 20 min, and then, 190 ml of the washed filtrate and 175 ml of the powder filtrate were taken respectively and then mixed and stirred to obtain 365 ml of mixed filtrate. The mixed filtrate, the washed filtrate and the powder filtrate were placed in the same thermostatic chamber and held at 30° C. for 16 min.

50 ml of the washed filtrate, 50 ml of the powder filtrate and 50 ml of the mixed filtrate were taken with a pipette respectively and added to three different Erlenmeyer flasks. 1.0 ml of potassium chromate solution with a mass fraction of 5% was dropped into each of the three Erlenmeyer flasks containing the washed filtrate, the powder filtrate and the mixed filtrate respectively. A silver nitrate titration method was used to obtain the mass of chloride ions in the washed filtrate as 0.256 g, the mass of chloride ions in the powder filtrate as 0.230 g and the mass of chloride ions in the mixed filtrate as 0.496 g, respectively. Then, the value of a was 0.980, and the chloride ions content in the sea sand was calculated to be 0.246% by using the method shown in Condition 2 according to the present invention.

Comparative Example 2

The chloride ions content in the sea sand was calculated according to the test method in GB/T 14684-2011 Sand for Construction. 1000 g of sea sand sample from the same source as the sea sand sample in the above application Embodiment 2 was dried to a constant weight in the oven and cooled for later use; 500 g of dry sand was weighed and poured into a ground-glass flask; 500 ml of distilled water was added into the ground-glass flask, which was then covered with a stopper, shook once and let stand for 2 h, and then, the ground-glass flak was shook once every 5 min, three times in total. A resulting solution was filtered and measured for the chloride ions content twice with a silver nitrate titration method, and an athematic mean value of the two test results was calculated to obtain the chloride ions content as 0.132%.

Embodiment 3

200 g of sea sand that was dried to a constant weight was poured into 500 ml of boiling deionized water, and then fully stirred for 6 min by using a magnetic stirrer at a revolving speed of 1000 r/min. The deionized water was continuously heated during stirring to be kept at the temperature of 95'. Upon completion of the stirring, the deionized water was let stand for 15 min and then filtered to obtain washed sea sand and 370 ml of washed filtrate. The washed sea sand was dried in an oven until the surface was free of water, and then ground into powder with a fineness of 120 meshes by using a ball mill. The powder was poured into 500 ml of deionized water, fully stirred for 6 min and then filtered to obtain 340 ml of powder filtrate. The washed filtrated and the powder filtrate were placed in a thermostatic chamber at 30° C. for 20 min, and then, 185 ml of the washed filtrate and 170 ml of the powder filtrate were weighed respectively and then mixed and stirred to obtain 355 ml of mixed filtrate. The mixed filtrate, the washed filtrate and the powder filtrate were placed in the same thermostatic chamber and held at 30° C. for 15 min.

50 ml of the washed filtrate, 50 ml of the powder filtrate and 50 ml of the mixed filtrate were taken with a pipette respectively and added to three different Erlenmeyer flasks. 1.0 ml of potassium chromate solution with a mass fraction of 5% was dropped into each of the three Erlenmeyer flasks containing the washed filtrate, the powder filtrate and the mixed filtrate respectively. A silver nitrate titration method was used to obtain the mass of chloride ions in the washed filtrate as 0.158 g, the mass of chloride ions in the powder filtrate as 0.126 g and the mass of chloride ions in the mixed filtrate as 0.255 g, respectively. Then, the value of a was 1.114, and the chloride ions content in the sea sand was calculated to be 0.284% by using the method shown in Condition 3 according to the present invention.

Comparative Example 3

The chloride ions content in the sea sand was calculated according to the test method in GBI/T14684-2011 Sand for Construction. 1000 g of sea sand sample from the same source as the sea sand sample in the above application Embodiment 3 was dried to a constant weight in the oven and cooled for later use. 500 g of dry sand was weighed and poured into a ground-glass flask. 500 ml of distilled water was added into the ground-glass flask, which was then covered with a stopper, shook once and let stand for 2 h, and then, the ground-glass flak was shook once every 5 min, three times in total. A resulting solution was filtered and measured in the chloride ions content twice with a silver nitrate titration method, and an athematic mean value of the two test results was calculated to obtain the chloride ions content as 0.154%.

From the above, it can be seen that the crushing of the sea sand can promote the release of the chloride ions in the tight-wrapping surface films and fissures of the sea sand; and meanwhile, the filtrate to be detected is prepared by using different methods before and after the sea sand is ground according to the present invention, which dissolves the chloride ions to a great extent while dramatically reducing the detection time and decreasing the detection errors of the chloride ions content.

The description above only provides the preferred embodiments of the present invention, but is not intended to limit the protection scope of the present invention. Any equivalent variations and modifications made by those skilled in the art within the technical scope disclosed by the present invention shall be construed as falling within the covering scope of the present invention.

What is claimed is:

1. A detection method for determining chloride ions content in sea sand, characterized by being performed in the steps as follows:
    Step 1, preparing a washed filtrate:
    drying a sea sand sample to be detected to constant weight, weighing the dried sea sand sample to be detected with a mass of $G_0$, then adding the dried sea sand sample to boiling deionized water, fully stirring for 3-6 min, letting stand for 10-15 min, and then filtering to obtain washed sea sand and a washed filtrate, wherein the deionized water is heated during stirring to keep the temperature not lower than 90° C., and a mass ratio of the dried sea sand sample to be detected for mixing and stirring to the deionized water is 1:(1.5-2.5);
    Step 2, preparing a powder filtrate:
    drying the washed sea sand from Step 1 until the surface of the sea sand is free of water, then grinding the washed sea sand into powder with a fineness of not less than 100 meshes, then adding the powder to deionized water, fully stirring for 5-10 min, and afterward, filtering to obtain a powder filtrate, wherein a mass ratio of the dried washed sea sand to the deionized water is 1:(1.5-2.5);
    Step 3, preparing a mixed filtrate:
    firstly, placing the washed filtrate prepared in Step 1 and the powder filtrate prepared in Step 2 in a thermostatic chamber, and letting stand for 15-20 min; then dividing the washed filtrate from Step 1 after standing into 2 equal parts separately, dividing the powder filtrate prepared in Step 2 after standing into 2 equal parts separately, and then mixing one part of the washed filtrate and one part of the powder filtrate to obtain a mixed filtrate, wherein the remaining part of the washed filtrate and the remaining part of the powder filtrate are for later separate use respectively;
    Step 4, measuring the mass of chloride ions in different filtrates:
    taking the mixed filtrate, the remaining part of the washed filtrate and the remaining part of the powder filtrate from Step 3 in same volume, and measuring the mass $H_1$ of chloride ions in the remaining part of washed filtrate, the mass $H_2$ of chloride ions in the remaining part of powder filtrate and the mass $H_3$ of the chloride ions in the mixed filtrate by using a silver nitrate titration method;
    Step 5, determining the chloride ions content in the sea sand:
    firstly, calculating the value of a, wherein a is the ratio of a sum of the mass $H_1$ of chloride ions in the remaining part of washed filtrate as measured in Step 4 and the mass $H_2$ of chloride ions in the remaining part of powder filtrate as measured in Step 4 to the mass $H_3$ of chloride ions in the mixed filtrate as measured in Step 4, i.e., $a=(H_1+H_2)/H_3$;
    then, when $0.850 \leq a \leq 1.150$, directly determining the chloride ions content Q in the sea sand according to the following three conditions; when the value of a is less than 0.850 or the value of a is greater than 1.150, repeating Step 4 and recalculating the value of a until $0.850 \leq a \leq 1.150$, and then determining the chloride ions content Q in the sea sand according to the following three conditions:
    Condition 1: when $0.850 \leq a < 0.975$, the total mass H of chloride ions in the sea sand is: $H=m(H_1+H_2)+H_3$; and then the chloride ions content Q in the sea sand is:

$$Q = \frac{m(H_1 + H_2) + H_3}{G_0} \times 100\%;$$

Condition 2: when $0.975 \leq a \leq 1.025$, the total mass H of chloride ions in the sea sand is: $H=H_1+H_2+H_3$; and then the chloride ions content Q in the sea sand is:

$$Q = \frac{H_1 + H_2 + H_3}{G_0} \times 100\%;$$

Condition 3: when $1.025 < a \leq 1.150$, the total mass H of chloride ions in the sea sand is: $H=H_1+H_2+nH_3$; and then the chloride ions content Q in the sea sand is:

$$Q = \frac{H_1 + H_2 + nH_3}{G_0} \times 100\%;$$

wherein m and n are coefficients, with $m=1+(1-a)=2-a$, and $n=1+(a-1)=a$.

2. The detection method for determining the chloride ions content in the sea sand according to claim 1, characterized in that, after the mixed filtrate is prepared in Step 3, the remaining part of the washed filtrate and the remaining part of the powder filtrate are placed in the same thermostatic chamber.

3. The detection method for determining the chloride ions content in the sea sand according to claim 1, characterized in that, when the masses of chloride ions in different filtrates are measured by using the silver nitrate titration method, a potassium chromate aqueous solution with a mass fraction of 5% is used as an indicator, and a ratio of a dropped volume of the potassium chromate aqueous solution in Step 4 to the volume of each of the mixed filtrate, the remaining part of the washed filtrate and the remaining part of the powder filtrate during titration is 1:50.

4. The detection method for determining the chloride ions content in the sea sand according to claim 1, characterized in that, a drying oven with a temperature of 100-110° C. is used for drying in Step 1 and Step 2; and the temperature of the thermostatic chamber is controlled to be 25-35° C. in Step 3.

5. The detection method for determining the chloride ions content in the sea sand according to claim 1, characterized in that, a magnetic stirrer is used for stirring in Step 1 and Step 2, wherein a revolving speed of the magnetic stirrer is 800-1500 r/min, and the maximum heating temperature of the magnetic stirrer is 120° C. during stirring.

* * * * *